(12) United States Patent
Helmer et al.

(10) Patent No.: US 12,048,836 B2
(45) Date of Patent: Jul. 30, 2024

(54) FORCE REDUCTION IN INJECTION DEVICES

(71) Applicant: SANOFI, Paris (FR)

(72) Inventors: Michael Helmer, Frankfurt am Main (DE); Stefan Wendland, Frankfurt am Main (DE)

(73) Assignee: Sanofi, Paris (FR)

( * ) Notice: Subject to any disclaimer, the term of this patent is extended or adjusted under 35 U.S.C. 154(b) by 955 days.

(21) Appl. No.: 17/048,010

(22) PCT Filed: Apr. 18, 2019

(86) PCT No.: PCT/EP2019/060195
§ 371 (c)(1),
(2) Date: Oct. 15, 2020

(87) PCT Pub. No.: WO2019/202128
PCT Pub. Date: Oct. 24, 2019

(65) Prior Publication Data
US 2021/0121634 A1    Apr. 29, 2021

(30) Foreign Application Priority Data
Apr. 19, 2018   (EP) ..................... 18305480

(51) Int. Cl.
*A61M 5/315* (2006.01)
*A61M 5/20* (2006.01)
(Continued)

(52) U.S. Cl.
CPC ...... *A61M 5/31501* (2013.01); *A61M 5/2033* (2013.01); *A61M 5/28* (2013.01);
(Continued)

(58) Field of Classification Search
CPC .. A61M 5/31501; A61M 5/2033; A61M 5/28; A61M 2005/2086;
(Continued)

(56) References Cited

U.S. PATENT DOCUMENTS 5,578,015 A * 11/1996 Robb .................... A61M 5/315
604/110
2002/0193736 A1   12/2002 Kiehne
(Continued)

FOREIGN PATENT DOCUMENTS

CN           1404403 A       3/2003
CN           1604799 A       4/2005
(Continued)

OTHER PUBLICATIONS

PCT International Preliminary Report on Patentability in International Application No. PCT/EP2019/060195, dated Oct. 20, 2020, 7 pages.
(Continued)

*Primary Examiner* — Jason E Flick
(74) *Attorney, Agent, or Firm* — Fish & Richardson P.C.

(57) ABSTRACT

This application relates to force reduction in injection devices. According to a first aspect, the specification describes an injection device comprising: a medicament container; a stopper translatably disposed within the medicament container; a plunger rod, the plunger rod comprising a plunger head; a drive mechanism for displacing the plunger rod into the medicament container; and a force reduction feature, wherein the plunger rod is operable to displace the stopper; and wherein the force reduction feature is arranged to damp at least a part of a plunger rod motion when the plunger rod is driven by the drive mechanism.

17 Claims, 11 Drawing Sheets

(51) Int. Cl.
  *A61M 5/28* (2006.01)
  *A61M 5/31* (2006.01)
(52) U.S. Cl.
  CPC .............. *A61M 2005/2086* (2013.01); *A61M 2005/3143* (2013.01)
(58) Field of Classification Search
  CPC .. A61M 2005/3143; A61M 2005/3151; A61M 5/31511; A61M 5/178; A61M 5/315; A61M 5/31513; A61M 2005/31521
  See application file for complete search history.

(56) References Cited

U.S. PATENT DOCUMENTS

| | | | |
|---|---|---|---|
| 2006/0178625 A1 | 8/2006 | Lim et al. | |
| 2009/0192486 A1 | 7/2009 | Wilmot et al. | |
| 2011/0071477 A1* | 3/2011 | Guillermo | A61M 5/31501 604/225 |
| 2012/0095408 A1* | 4/2012 | Eaton | A61M 5/3272 604/218 |
| 2013/0296795 A1 | 11/2013 | Ekman et al. | |
| 2016/0144135 A1 | 5/2016 | Taal et al. | |
| 2017/0182253 A1 | 6/2017 | Folk et al. | |
| 2017/0246394 A1 | 8/2017 | Cabiri | |

FOREIGN PATENT DOCUMENTS

| | | |
|---|---|---|
| CN | 105530969 A | 4/2016 |
| EP | 2080532 | 7/2009 |
| EP | 2399627 | 12/2011 |
| JP | 2009-540875 A | 11/2009 |
| JP | 2012-525185 A | 10/2012 |
| JP | 2013-529519 A | 7/2013 |
| JP | 2017-518791 A | 7/2017 |
| WO | WO 2007/130388 A2 | 11/2007 |
| WO | WO 2011/012849 A1 | 2/2011 |

OTHER PUBLICATIONS

PCT International Search Report and Written Opinion in International Application No. PCT/EP2019/060195, dated May 28, 2019, 9 pages.

* cited by examiner

FORCE REDUCTION IN INJECTION DEVICES

CROSS REFERENCE TO RELATED APPLICATIONS

The present application is the national stage entry of International Patent Application No. PCT/EP2019/060195, filed on Apr. 18, 2019, and claims priority to Application No. EP 18305480.8, filed on Apr. 19, 2018, the disclosures of which are incorporated herein by reference.

TECHNICAL FIELD

This application relates to force reduction in injection devices. More particularly, the present application relates to injection devices having a force reduction component that reduces the net force of a drive mechanism on a plunger of the injection device.

BACKGROUND

Auto injector injection devices usually comprise a drive mechanism that is used to depress a plunger in the injection device in order to expel a medicament from them. Depending on the properties of the medicament to be expelled (such as the filling level of the medicament cartridge, the medicament density and dose, and the correlated gliding force of the primary pack), the force applied to plunger by the drive should be varied to prevent damage to the injection device by the impact force of the injection device plunger on the syringe stopper of the injection device. Furthermore, a high impact force on the stopper can result in a negative user experience when using the injection device. For example, the impact force may cause pain to the user, and/or the injection may occur too quickly.

SUMMARY

According to a first aspect, the specification describes an injection device comprising: a medicament container; a stopper translatably disposed within the medicament container; a plunger rod, the plunger rod comprising a plunger head; a drive mechanism for displacing the plunger rod into the medicament container; and a force reduction feature, wherein the plunger rod is operable to displace the stopper; and wherein the force reduction feature is arranged to damp at least a part of a plunger rod motion when the plunger rod is driven by the drive mechanism.

The force reduction feature may be configured to damp the plunger rod motion for at least a part of the displacement of the stopper.

The force reduction may comprise a bore through which the plunger rod can pass.

The bore may have compressible walls, which are compressible by the plunger head as the plunger head passes through the bore.

The bore may be tapered.

The medicament container, the stopper and the reduction feature may define a cavity, the cavity having a cavity length that is less than a plunger head length.

The plunger head may comprise one or more grooves extending around the plunger head and the force reduction feature comprises one or more pins engageable with the one or more grooves on the plunger head thereby to rotate the plunger head as the plunger is displaced into the medicament container.

The plunger head may comprise a rotatable nut around which the grooves extend.

The force reduction feature may comprise an O-ring mounted on the plunger head, and the O-ring may be arranged to roll along the plunger head when the plunger is displaced into the medicament container.

The O-ring may be arranged to roll off of the plunger head after a predetermined displacement distance of the plunger into the medicament container.

The force reduction feature may comprise a chamfered head on the plunger head and a deformable chock on the stopper for receiving the chamfered head, wherein the deformable chock is arranged to expand upon receiving the chamfered head, thereby to grip walls of the medicament container.

The force reduction feature may comprise one or more indentations on the plunger rod and one or more flexible arms on the injection arranged to catch the one or more indentations on the force reduction head.

The injection device may further comprise a medicament stored within the medicament container.

BRIEF DESCRIPTION OF THE FIGURES

Example embodiments will now be described by way of non-limiting example with reference to the accompanying drawings, in which.

DETAILED DESCRIPTION

Figure 1:
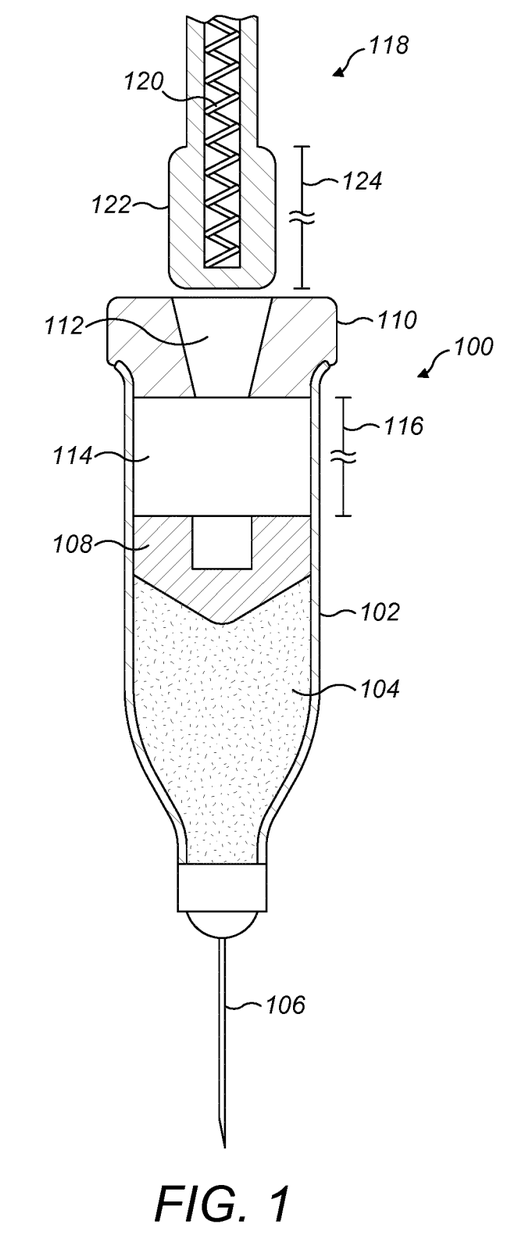
FIG. 1 shows a schematic example of an injection device with a force reduction feature comprising a compressible bore.

FIG. 1 shows a schematic example of an injection device with a force reduction feature. The injection device 100 comprises a medicament container 102 for retaining a medicament 104. In the embodiment shown, the medicament container 102 forms part of a syringe (for one shot devices, for example). In other embodiments, the medicament container 102 forms a part of an auto-injector. In such cases, the medicament container 102 may be a consumable part of the auto-injector capable of being replaced as required, for example a medicament cartridge. In the embodiment shown, the walls of the medicament container 102 are substantially cylindrical. In general, the medicament container 102 can have a different cross sectional shape.

The injection device 1 further comprise a needle 106 via which the medicament 104 can be expelled from the medicament container 102. The needle 106 is, in some embodiments, an integral part of the medicament container 102. In other embodiments, the needle 106 is part of an autoinjector pack into which the medicament container can be inserted. In the following, the needle 106 end of the injection device 100 will be referred to as the distal end, with the opposite end of the injection 100 device referred to as the proximal end.

A stopper 108 is translatably disposed between the walls of the medicament container 102. The stopper 108 is translatable in the axial direction of the medicament container 102.

A force reduction feature (also referred to herein as a "reduction feature") 110 is provided at the proximal end of the medicament container 102. In embodiment shown, the reduction feature 110 is provided in the form of a cap for the medicament container 102. In other embodiments, the force reduction feature 110 can be provided as part of an autoinjector. The reduction feature 110 is mounted on the open end of the medicament container 102. In the example shown, the reduction feature 110 comprises a bore 112 through its centre that fluidly connects a cavity 114 inside the medicament container 102 to the outside of the medicament container 102. In the example shown the bore 112 is tapered inwardly into the medicament container 102. The reduction feature 110 is mounted on the proximal end of the medicament cartridge 102, for example by being composed of an elastic material that is retained by the inside wall of the medicament container 102. The reduction feature 110 may be mounted to the medicament container 102 using a transition fit.

The reduction feature 110 bore 112 walls are formed from a compressible material. For example, rubber or plastic can be used.

The reduction feature 110, stopper 108 and medicament container 102 walls define a cavity 114 at the proximal end of the medicament container 102. The cavity has an initial cavity length 116 ($S_2$) that depends on the position of the stopper 108 within the medicament container 102. The cavity 114 therefore also has a variable initial cavity volume.

A plunger 118 (herein also referred to as a plunger rod or piston rod) is provided which can be depressed into the medicament container 102 in order to expel the medicament 104 via the needle 106. The plunger 118 may be manufactured from plastic or metal, for example. The plunger 118 is displaceable in the axial direction of the medicament container 102. When depressed towards the distal end of the medicament container 102, the plunger 118 enters the cavity 114 of the medicament container though the bore 112 in the reduction feature 110. The plunger 118 acts to displace the stopper 108 towards the needle 106, thereby expelling the medicament 104 from the medicament container 102 via the needle 106. The plunger 118 is displaced into the medicament container 102 by means of a drive mechanism 120. In the embodiment shown, the drive mechanism 120 comprises a spring located within the plunger rod. In embodiments using an auto-injector, the plunger 118 is mounted in and/or driven by an auto-injector powerpack.

The plunger 118 comprises a plunger head 122 at the distal end of the plunger. The plunger head 122 has an axial length 124 ($S_1$) over which the diameter of the plunger head 122 is greater than the diameter of at least a portion of the bore 112. This can allow the plunger rod 118 motion to be damped by providing resistance to the plunger rod 118 motion as it passes through the bore 112, thereby reducing the net force on the plunger rod 118.

The amount of force reduction provided by the cooperation of the plunger head 122 and the bore 112 can be varied in several ways. One example is varying the axial length 124 of the plunger head 122. This changes the influence of the plunger head 122 on the drive mechanism 120 working area (stroke). The diameter of the plunger head 122 can also be varied to vary the amount of force reduction applied to the plunger 118 by the bore 112. The length of the plunger head 122 is equal to the length of the primary pack upper dead volume. The plunger head will therefore be released by the bore 112 when the force reduction head 122 is in contact with the stopper.

Another example is varying the geometry and/or the material (e.g. to vary the Shore hardness) of the force reduction feature 110. For example, varying the diameter of the bore 112 and/or varying the taper of the bore 112 can change the amount of force reduction applied. As an example, a narrower diameter of the bore 112 can result in a greater force reduction. By providing a means for varying the force reduction (by, for example, varying the bore 112 properties), the same drive mechanism 120 can be used for different medicament container 102 fill levels, drug densities and/or the correlated gliding forces. This can simplify the design of the injection devices.

The plunger head 122 has, in this embodiment, an axial length 124 equal to or greater than the initial cavity length 116 (i.e. $S_1 \geq S_2$) so that the plunger rod 118 motion is being damped or just released from being damped as it contacts the stopper 108.

In some embodiments (not shown), the plunger head 122 is formed from a compressible material, such as rubber or plastic for example. In these alternative embodiments, the force reduction feature 110 bore 112 may be formed from either a compressible or an incompressible material.

Figure 2A:
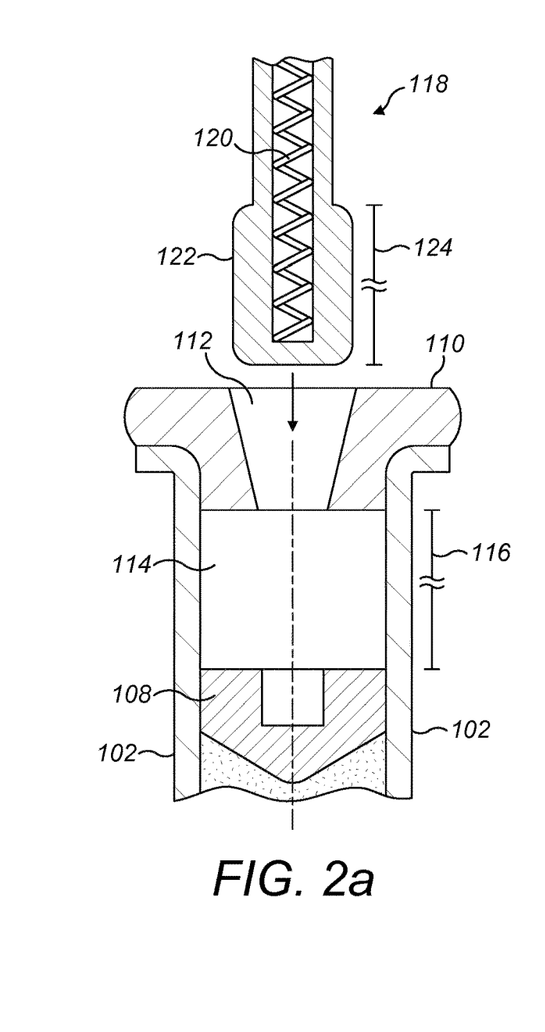
FIGS. 2*a-c* show schematic examples of an injection device with a force reduction feature in use.
Figure 2B:
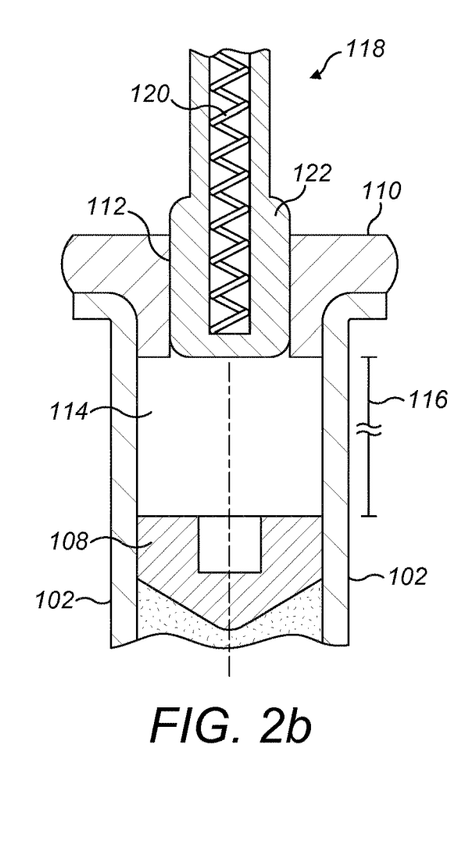
Figure 2C:
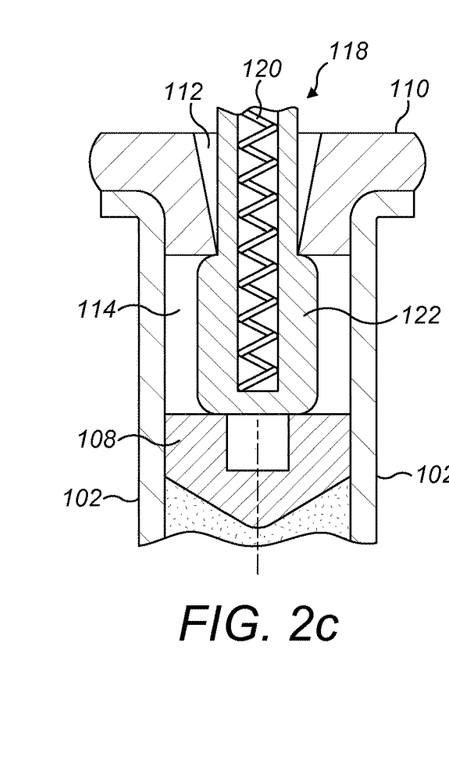

FIGS. 2a-c show schematic examples of an injection device with a force reduction feature 110 in use. With reference to FIG. 2a, the plunger 118 is initially completely outside of the medicament container 102. A user initiates an injection by, for example, pressing a button on an auto-injector pack. This actuates the drive mechanism 120 to depress the plunger 118 into the medicament container 102 via the bore 112 in the force reduction feature 110.

With reference to FIG. 2b, as the drive mechanism 120 depresses the plunger 118 into the medicament container 102 cavity 114 the plungerhead 122 passes through the bore 112 of the cap 110. The plungerhead 122 compresses the walls of the bore 112 as it moves through the bore 112. This retards the motion of the plunger rod 118 by providing resistance to the plunger rod 118 motion, thereby reducing the net force on the plunger rod 118.

With reference to FIG. 2c, as the plunger 118 is depressed further into the cavity 114 of the medicament container 102, the plunger head will eventually come into contact with the stopper 108. As the axial length 124 is equal to or greater than the initial cavity length 116 (i.e. $S_1 \geq S_2$), the bore 112 walls will still be compressed by a portion of the plunger head 122 (or, as in the example shown, just have released the force reduction head) at this moment, reducing the net force on the plunger 118. The impact force of the plunger 118 on the stopper 108 is therefore reduced.

This allows an injection device to use one spring with the highest possible load for multiple different medicament indications.

Figure 3A:
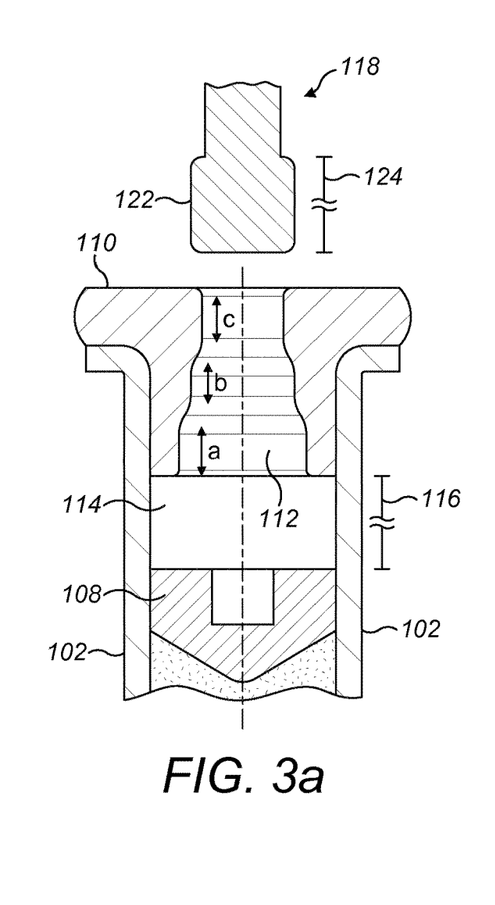
FIGS. 3*a-c* show schematic examples of alternative embodiments an injection device with a force reduction feature comprising a compressible bore.
Figure 3B:
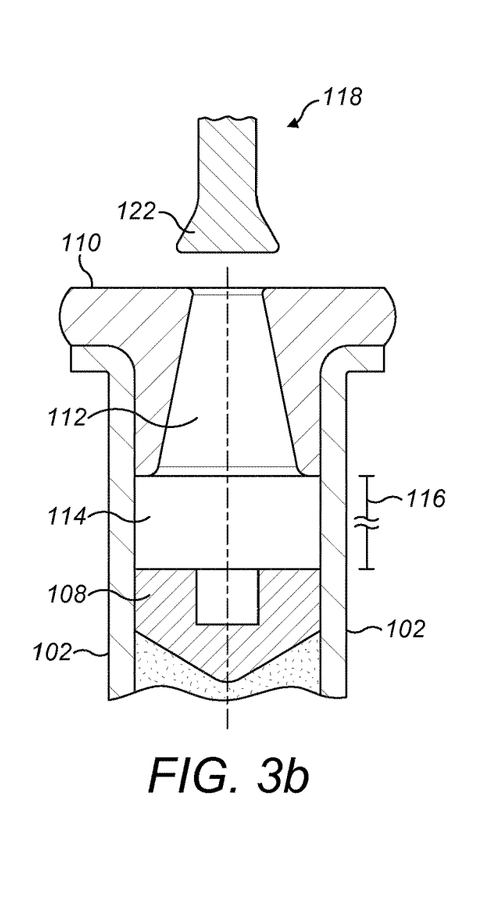
Figure 3C:
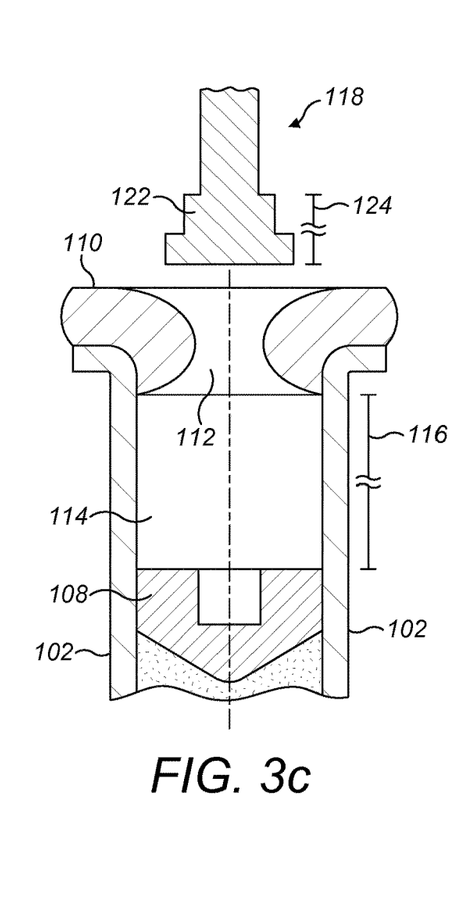

FIGS. 3a-c show schematic examples of alternative embodiments an injection device with a force reduction feature comprising a compressible bore.

In the embodiment shown FIG. 3a, the force reduction feature 110 comprises a central bore 112 comprising a series of one or more step-changes in the bore 112 diameter. In the example shown, there are two step changes in the bore diameter, though fewer or more step changes can be used. The bore diameter is narrowest at the proximal end of the medicament cartridge, with the step changes increasing the bore diameter as the bore 112 progresses into the cavity 114 of the medicament container 102. The lower, middle and upper stepped portions of the bore 112 have lengths a, b and c respectively. In some embodiments, the length of the plunger head 122 is equal to or greater than the total length of the bore (a+b+c). Having stepped portions can vary the amount of resistance to the plunger motion as the plunger head 122 progresses through the bore 112. This can be beneficial when the plunger 118 is driven by a spring.

In the embodiment shown FIG. 3b, the cap 110 comprises a central bore 112 that tapers in the axial direction of the medicament cartridge 112. In contrast to the embodiment of FIG. 1, the bore diameter increases as the bore 112 progresses into the cavity 114 of the medicament container 102. In this embodiment, the plunger head 122 is also tapered, being wider at the distal end of the plunger head 122 than the proximal end. This can lead to a smoother release of the plunger rod by the reduction feature.

In the embodiment shown in FIG. 3c, the cap 110 comprises a shallow central bore 112 that is untapered. The plunger head 122 comprises a series of steps in diameter. Having stepped portions can vary the amount of resistance to the plunger motion as the plunger head 122 progresses through the bore 112. This can be beneficial when the plunger 118 is driven by a spring.

Figure 4:
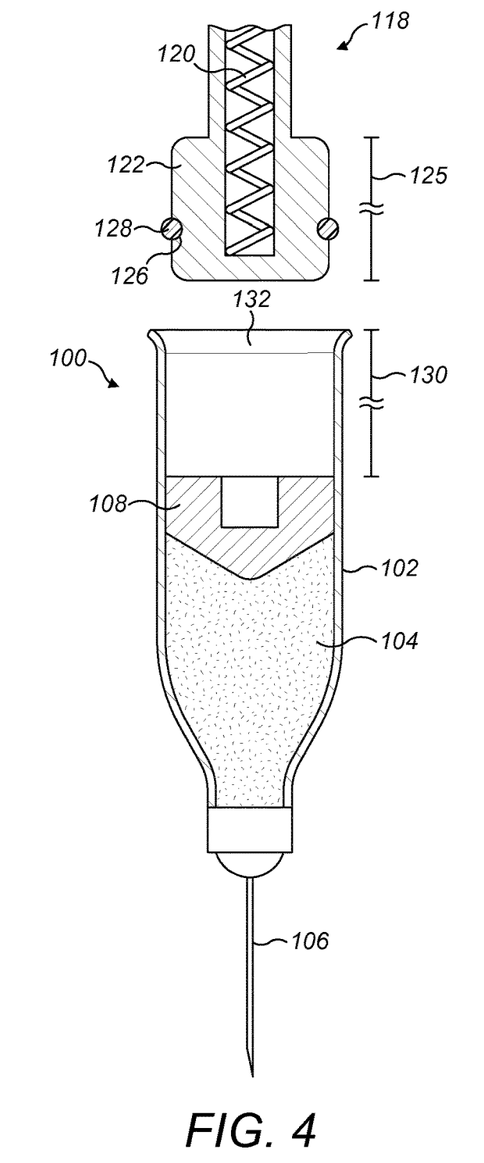
FIG. 4 shows a further embodiment of an injection device with a force reduction feature comprising an O-ring.

FIG. 4 shows a further embodiment of an injection device with a plunger head 122 comprising an O-ring. In this embodiment, the injection device 100 comprises a medicament cartridge 102, medicament 104, needle 106 and stopper 108 as described in relation to FIG. 1. The injection device 100 is provided with a plunger 118 comprising a drive mechanism 120, also as described in relation to FIG. 1. The stopper 108 and the opening 132 of the medicament container define a length $S_3$ 130. In the embodiment shown, no bored force reduction feature is provided. In other embodiments a bored force reduction feature, as disclosed in any of the capped embodiments described herein, can be provided. In some embodiments, a stopper 108 with a tapered bore can be used.

The plunger 118 comprises a plunger head 122. The plunger head 122 comprises a force reduction feature in the form of a groove 126 into which an O-ring 128 is fitted. The groove 126 is located towards the distal end of the plunger head. The plunger head 122 has a length 125 in the axial direction from the groove 126 to the proximal end of the plunger head of $S_4$. In some embodiments $S_4 \geq S_3$.

The O-ring 128 can be manufactured from an elastic material, such as rubber. The material and/or the O-ring 128 thickness can be varied to vary the reduction force applied during operation of the plunger 118.

Figure 5A:
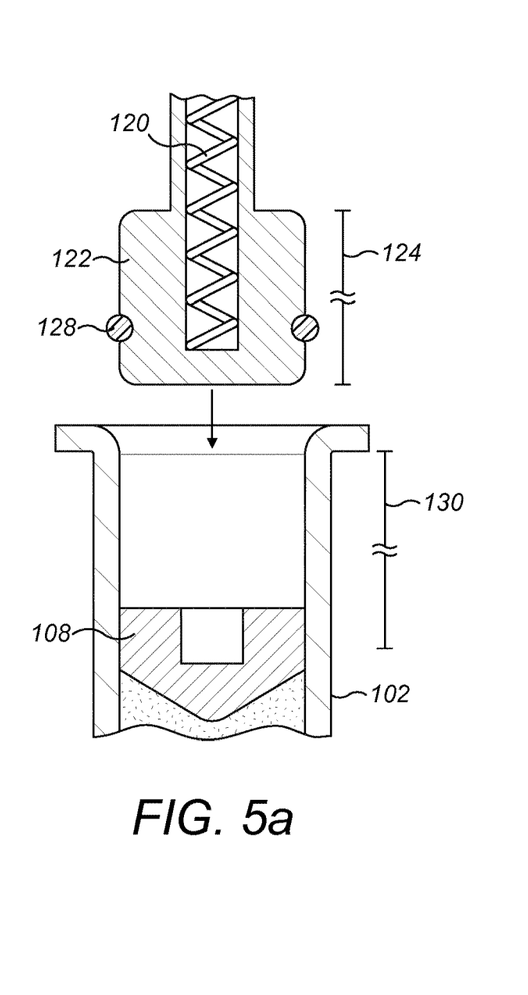
FIGS. 5*a-c* show schematic examples of an injection device with a force reduction feature comprising an O-ring in use.
Figure 5B:
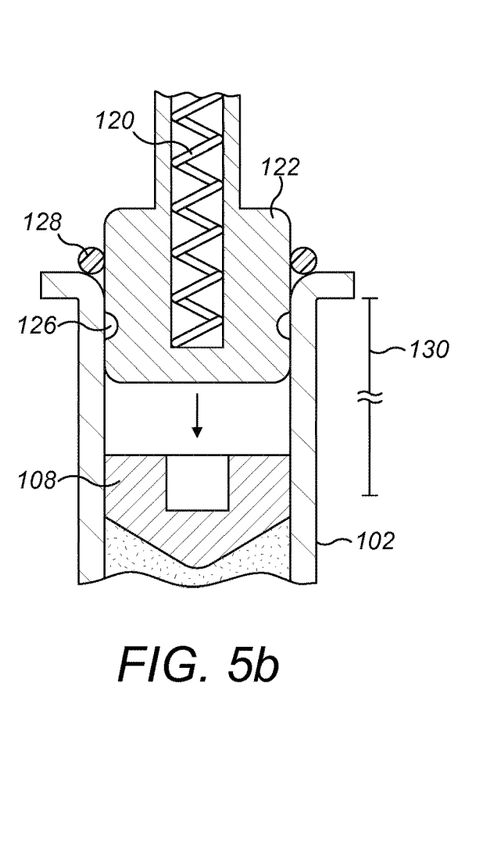
Figure 5C:
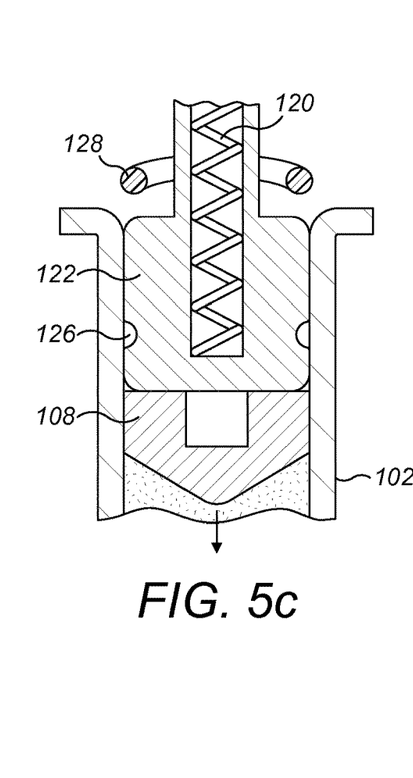

FIGS. 5a-c show schematic examples of an injection device with a force reduction head comprising an O-ring in use.

With reference to FIG. 5a, the plunger 118 is initially completely outside of the medicament container 102. A user initiates an injection by, for example, pressing a button on an auto-injector pack. This actuates the drive mechanism 120 to depress the plunger 118 into the medicament container 102.

With reference to FIG. 5b, as the plunger 118 is depressed into the medicament cartridge, the O-ring 128 catches on the lip of the medicament container 102. As the plunger 118 is depressed further into the medicament cartridge 102, the O-ring 128 rolls along the plunger head length 130, which provides resistance to the plunger 118 motion.

With reference to FIG. 5c, continued depression of the plunger 118 by the drive mechanism 120 results in the plunger head 122 coming into contact with the stopper 108. The stopper 108 will then be displaced towards the distal end of the injection device 100, thereby expelling medicament 104 via the needle 106. In embodiments where $S_1 \geq S_3$, the O-ring 128 is still retarding the motion of the plunger as the plunger head 122 makes contact with the stopper 108, thereby reducing the initial force on the stopper 108.

As the plunger 118 continues to be depressed, the O-ring 128 reaches the end of the plunger head length 130. The rest of the plunger 118 has a narrower diameter than the plunger head 122, and the O-ring 128 can therefore contract away from the lip of the medicament container 102. In this position, the O-ring 128 ceases to retard the motion of the plunger 118.

Figure 6:
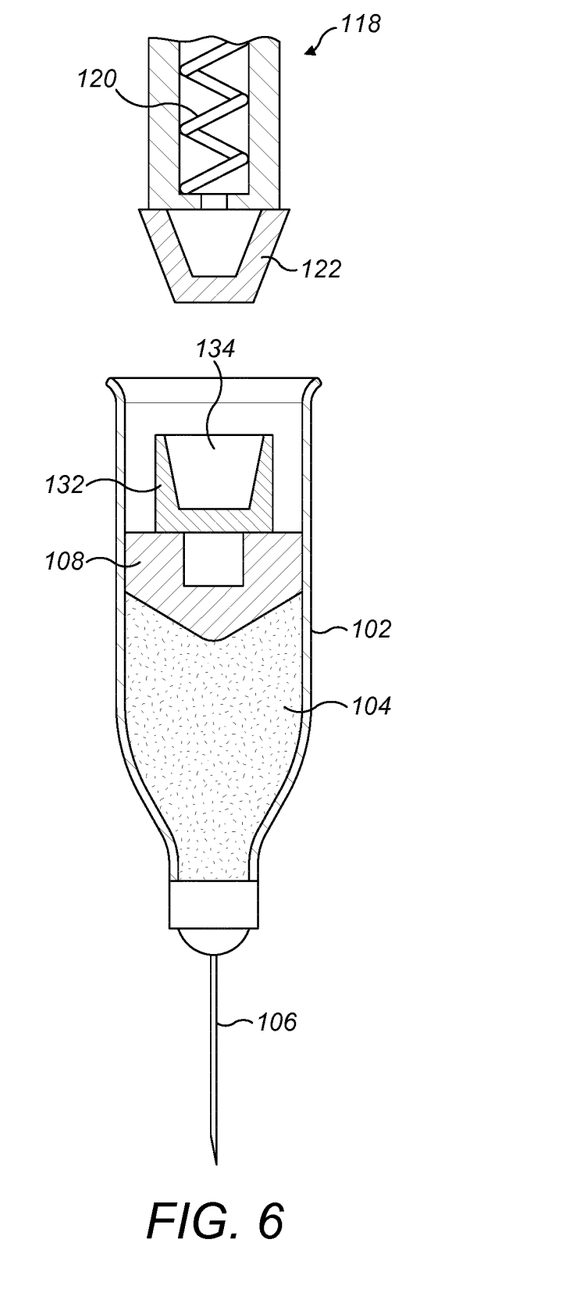
FIG. 6 shows a further embodiment of an injection device with a chock and chamfered plunger head force reduction feature.
Figure 7:
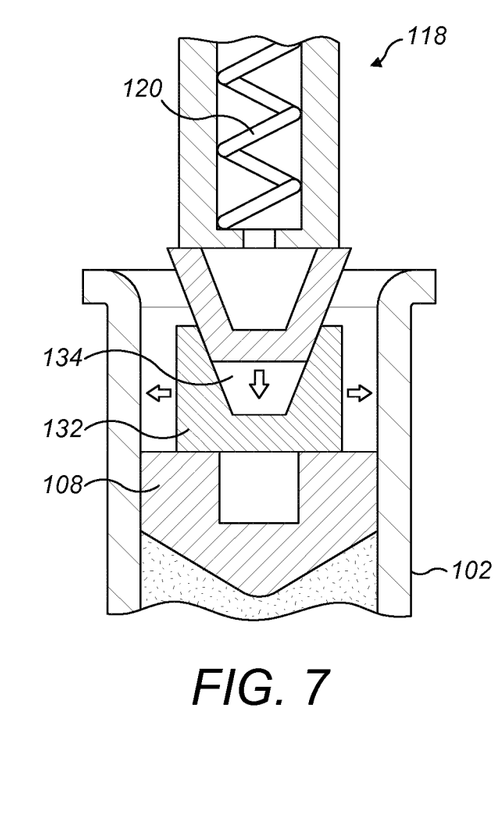
FIG. 7 shows an example of the injection device with a chock and chamfered plunger head in use.

FIG. 6 shows a further embodiment of an injection device with a chock and chamfered force plunger head. FIG. 7 shows an example of the injection device with a chock and chamfered plunger head in use.

In these embodiments, the plunger head 122 is chamfered such that it reduces in diameter towards the needle end of the injection device 100. The stopper 108 comprises a deformable chock 132 into which the plunger head 122 can be received. The deformable chock 124 comprises a central recess 134 to receive the force reduction head 122. The central recess 134 has chamfered walls. The plunger head 122 has a larger volume than the central recess 134 of the deformable chock 122. This causes the deformable chock 132 to deform when the plunger head 122 is received by the central recess 134. The deformable chock can be manufactured from a material comprising a rubber or plastic material, for example TPE or PP.

As the drive mechanism 120 drives the plunger into contact with the stopper 108, the plunger head 122 is driven into the central recess 134 of the deformable chock 132. The difference in the volumes between the plunger head 122 and the central recess 134 causes the deformable chock 132 to deform outwardly.

The deformable chock 132 is arranged such that the deformation caused by the plunger head 122 entering the recess 134 causes the side walls of the deformable chock 132 to contact the inside surface of the medicament cartridge walls. The force of the deformable chock 132 against the medicament cartridge walls acts to decelerate the plunger 118 and reduces the total force on the plunger 118 over the complete injection stroke. The deformable chock 134 is designed in such a way that a surface pressure between the medicament cartridge wall and the deformable chock exists when the plunger rod is driven into the chock, which can act to prevent glass breakage.

The chamfered plunger head 122 and the deformable chock 132 therefore cooperate to provide a force reduction feature.

Figure 8:
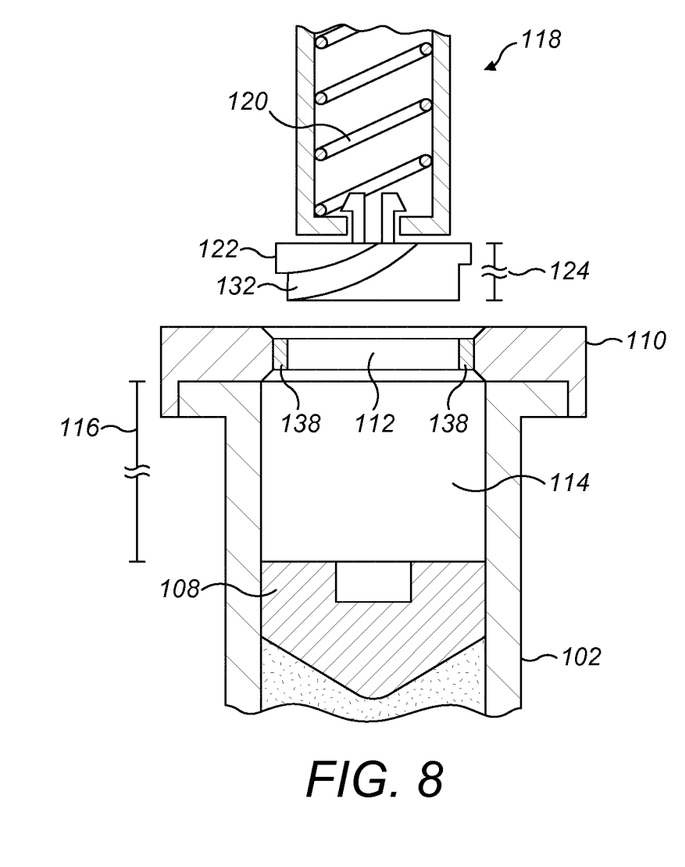
FIG. 8 illustrates an example of an injection device having a rotatable nut on the plunger rod.
Figure 9:
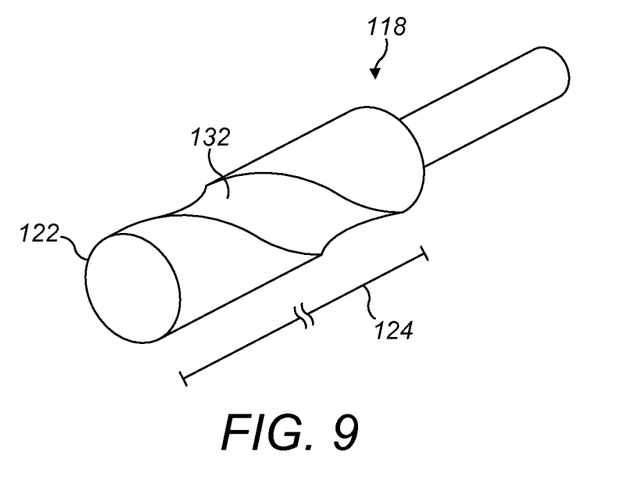
FIG. 9 shows a perspective view of the plunger rod of FIG. 8.

FIG. 8 illustrates an example of an injection device having a rotatable nut on the plunger rod. FIG. 9 shows a perspective view of the plunger rod of FIG. 8. In this embodiment, the plunger head 122 comprises a rotatable pitch nut. The pitch nut comprises one or more groves 136 that wind around the axial direction of the force reduction head 122 body. The plunger has a length in the axial direction 124 of $S_1$ (not shown to scale in FIGS. 8 and 9). The grooves 138 extend along this length. The remaining body of the plunger has a radius less than that of the grooves 132 of the plunger head 122.

The injection device cap 110 comprises a central bore 112 with one or more pins 138 (in the example shown, there are two pins) extending inwardly into the bore from the bore edge. The pins 138 are engageable with the one or more grooves 136 winding around the plunger head 122, and act as "counter bearings". The cap 110, stopper 108 and medicament container 102 walls define a cavity 114 with a cavity length 116 of $S_2$ (not shown to scale).

In use, the drive mechanism 120 (which in the example shown is a spring) drives the plunger 118 into the medicament container 102 via the bore 112 in the cap 110. As it does so, the grooves 136 in the plunger head 122 engage with the pins 138 extending into the bore 112 of the cap 110. This provides resistance to the motion of the plunger 118. As the plunger 118 is depressed further by the drive mechanism 120, the plunger head 122 rotates relative to the plunger 118 main body and the medicament container 102, effectively "screwing" into the bore. This provides resistance to the plunger motion. As the plunger 118 is depressed even further, the pins 138 will eventually reach the end of the grooves 136 and exit them. A damping force will then no longer be applied to the plunger 118 by the pins 136.

Where $S_1 \geq S_2$ the plunger head 122 will be rotating as it makes contact with the stopper 108, thereby reducing the initial impact force of the plunger 118 on the stopper 108. The cooperation of the plunger head grooves 136 and pins 138 thereby provides a force reduction feature.

Figure 10:
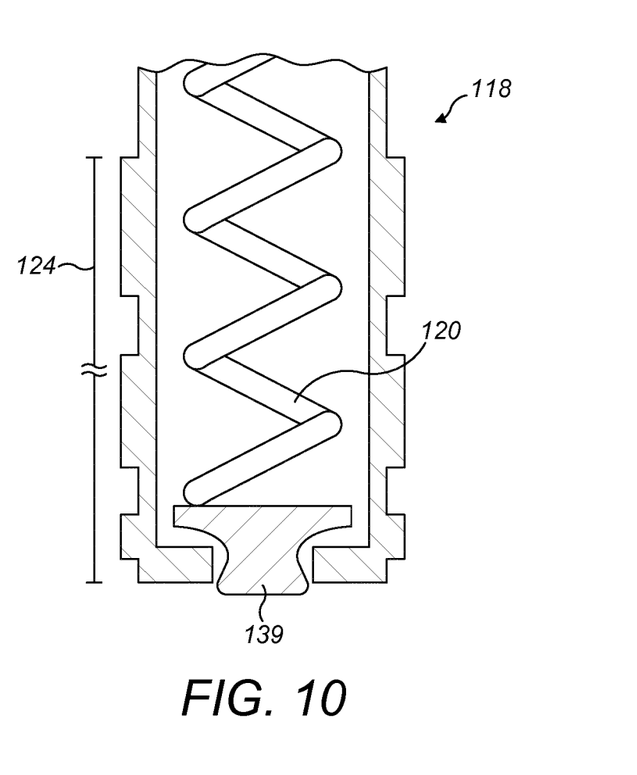
FIG. 10 shows an alternative embodiment of a force reduction feature for use in embodiments of injection devices as described in FIG. 8.

FIG. 10 shows an alternative embodiment of a plunger head for use in embodiments of injection devices as described in FIG. 8. In this embodiment, the plunger head 122 is fixed relative to the main body of the plunger, and the plunger rod 118 as a whole rotates as the plunger rod 118 is driven into the medicament container 102 by the drive mechanism 120. In embodiments where the drive mechanism 120 is a spring, a rotary plate 139 is provided inside the plunger head 122 on which the spring rests. The rotary plate 139 allows the plunger rod 118 to rotate around the spring without twisting the spring.

When the plunger 118 is driven into the medicament cartridge, the pins 138 and the grooves 132 cause the plunger 118 to rotate, reducing the forces on the plunger rod 118 and its speed. The plunger rod 118 has a lead-in pitch to the grooves 132 to ensure connectivity between the grooves 132 and the pins 138. The gradient of the grooves 132 corresponds to the required force and speed reduction.

Figure 11:
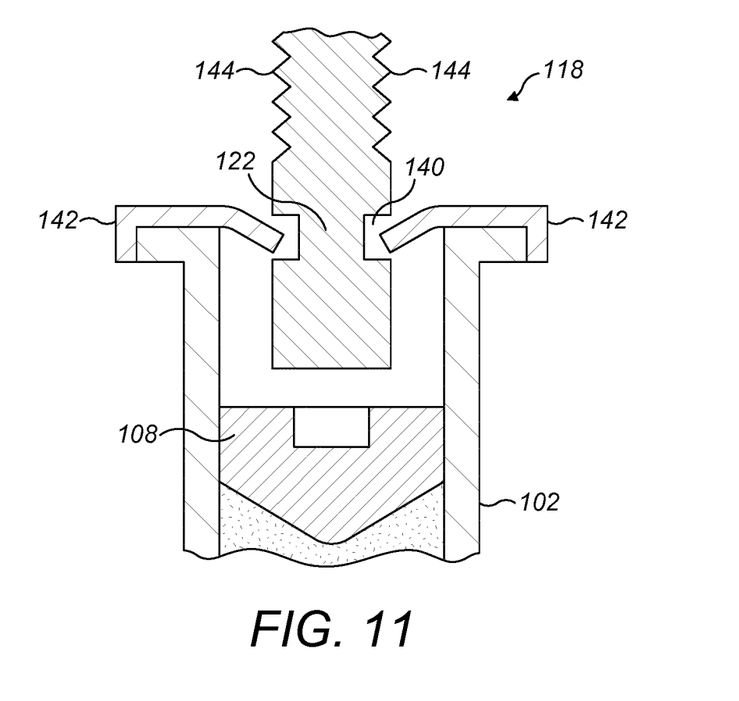
FIG. 11 shows a schematic of a further embodiment of an injection device with a force reduction feature comprising a plurality of flexible arms.
Figure 12:
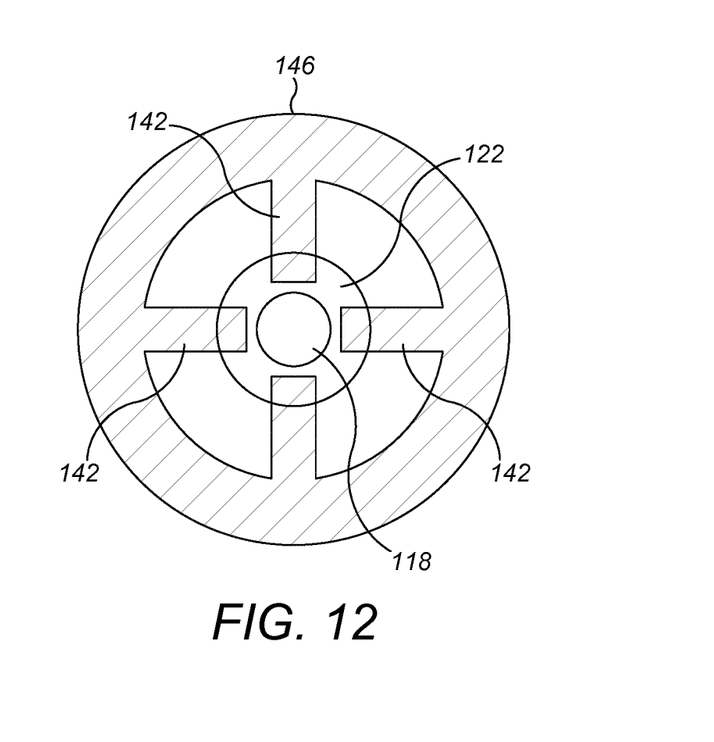
FIG. 12 shows a top view of the plunger and flexible arms.

FIG. 11 shows a schematic of a further embodiment of an injection device with a plunger head comprising a plurality of flexible arms. FIG. 12 shows a top view of the plunger and flexible arms. In this embodiment, the plunger head comprises one or more indentations 140. The injection device comprises one or more flexible arms 142 which engage with the indentations 140 on the plunger head 122. In the embodiment shown, 4 flexible arms 142 are provided, though a fewer or greater number of arms can be used. The flexible arms 142 may be provided as a part of the medicament cartridge 102, for example as part of a cap or integrated with the medicament cartridge 102. Alternatively, the flexible arms 140 can be provided as part of a separate syringe drive plate 146, as shown in FIG. 10. The flexible arms 140 can, for example, be manufactured from stamped metal.

In some embodiments, the plunger rod 118 further comprises one or more serrations 144 arranged to catch the flexible arms 140 as the plunger is depressed into the medicament cartridge 102, thereby providing additional resistance/damping to the plunger rod 118 motion. The serrations 144 can, in some embodiments, extend along the full length of the plunger rod 118, thereby providing damping to the plunger rod 118 motion throughout the whole of an injection event. The serrations 144 catching on the flexible arms 140 can also provide audible feedback to the user.

When the plunger 118 is driven into medicament cartridge 102, the flexible arms caught in the indentation flex, applying a force to the plunger head 122 that opposes its motion. The plunger rod 118 motion is thereby damped. As the plunger rod 118 is depressed further into the medicament cartridge, the flexible arms are increasingly flexed, until eventually they release the plunger rod. The cooperation of the indentations and the flexible arms provides a force reduction feature.

Figure 13:
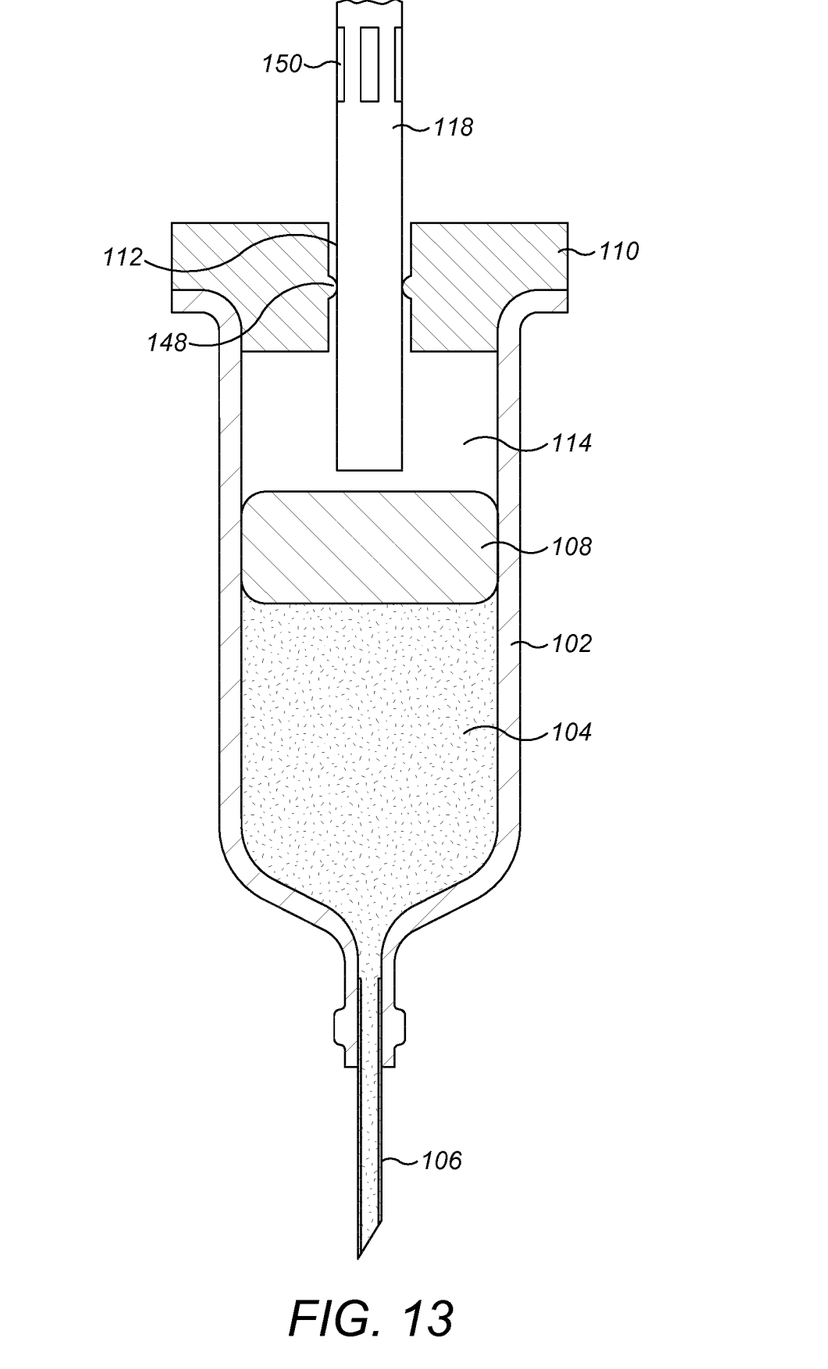
FIG. 13 shows an embodiment of an injection device with a force reduction feature comprising a flexible lip.
Figure 14:
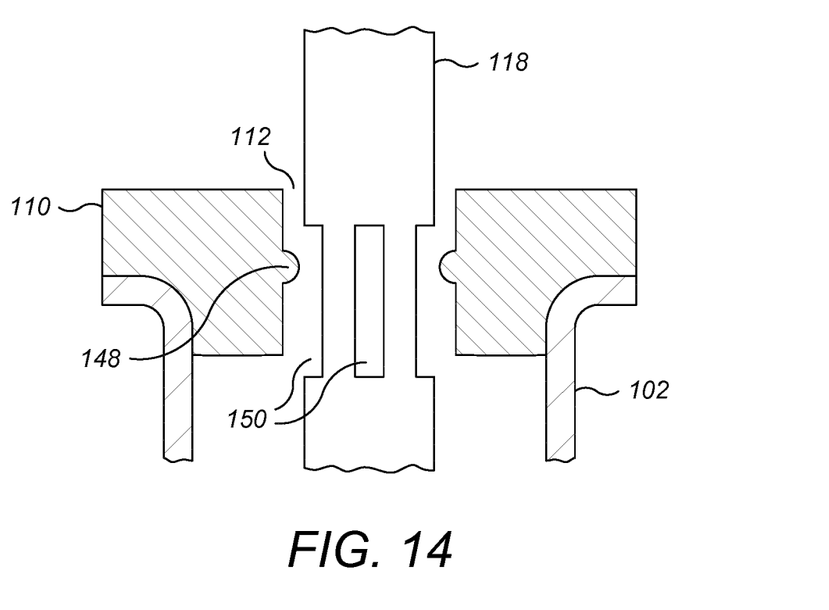
FIG. 14 shows an embodiment of an injection device with a force reduction feature comprising a flexible lip.

FIGS. 13 and 14 show an embodiment of an injection device with a force reduction feature comprising a flexible lip.

In this embodiment, the cap 110 comprises a bore 112 have a flexible lip 148. The flexible lip 148 is arranged to grip the plunger rod 118 as it passes into the medicament container 102. The flexible lip 148 provides additional resistance to the plunger rod 118 motion, acting as a force reduction feature.

The flexible lip 148 forms a substantially airtight seal with the plunger rod 118.

In some embodiments, the flexible lip 148 is arranged to grip a plunger head (not shown in FIG. 13) on the plunger rod 118. The plunger head has a greater diameter than the rest of the plunger body. Once the plunger head has passed the flexible lip, the plunger rod 118 is no longer in contact with the flexible lip, and the plunger rod 118 motion is no longer retarded by the flexible lip 148.

In other embodiments, the plunger rod 118 comprises one or more slits 150 in the plunger rod body at a predefined distance along the plunger rod 118, such that the flexible lip 148 releases the plunger rod 118 as the slits 150 pass across the flexible lip 148, as illustrated in more detail in FIG. 14. Therefore a force reduction is applied to the plunger rod 118 for the length of the plunger rod 118 between its distal end and the position of the slits 150.

Two or more of the force reduction features described above may be combined into a single force reduction feature. For example, a compressible bore may also be supplied with an O-ring on the corresponding plunger head, with both the bore being compressed and the O-ring being displaced as the force reduction head passes into the medicament cartridge.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin. Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ωoxyheptadecanoyl)-des(B30) human insulin and B29-N-(ωoxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present embodiments include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. An injection device comprising:
   a medicament container;
   a stopper translatably disposed within the medicament container;
   a plunger rod comprising a plunger head, wherein the plunger head comprises one or more grooves extending around the plunger head;
   a drive mechanism for displacing the plunger rod into the medicament container; and
   a force reduction feature,
   wherein the plunger rod is operable to displace the stopper,
   wherein the force reduction feature is arranged to damp at least a part of a motion of the plunger rod when the plunger rod is driven by the drive mechanism, and
   wherein the force reduction feature comprises one or more pins engageable with the one or more grooves on the plunger head thereby to rotate the plunger head as the plunger rod is displaced into the medicament container.

2. The injection device of claim 1, wherein the force reduction feature is configured to damp the plunger rod motion for at least a part of the displacement of the stopper.

3. The injection device of claim 1, wherein the force reduction feature comprises a bore through which the plunger rod can pass.

4. The injection device of claim 3, wherein the bore has compressible walls that are compressible by the plunger head as the plunger head passes through the bore.

5. The injection device of claim 3, wherein the bore is tapered.

6. The injection device of claim 3, wherein the medicament container, the stopper, and the force reduction feature define a cavity.

7. The injection device of claim 1, wherein the force reduction feature comprises an O-ring mounted on the plunger head.

8. The injection device of claim 7, wherein the O-ring is arranged to roll along the plunger head when the plunger rod is displaced into the medicament container.

9. The injection device of claim 1, wherein a chamfered head on the plunger head and a deformable chock on the stopper for receiving the chamfered head are configured to cooperate to provide the force reduction feature.

10. The injection device of claim 1, wherein one or more indentations on the plunger rod and one or more flexible arms arranged to catch the one or more indentations on the plunger rod are configured to cooperate to provide the force reduction feature.

11. The injection device of claim 1, wherein the drive mechanism comprises a spring.

12. The injection device of claim 1, further comprising a needle.

13. The injection device of claim 1, further comprising a medicament stored within the medicament container.

14. The injection device of claim 6, wherein the cavity has a length that is equal to or less than a length of the plunger head.

15. The injection device of claim 1, wherein the plunger head comprises a rotatable nut around which the one or more grooves extend.

16. The injection device of claim 8, wherein the O-ring is arranged to roll off of the plunger head after a predetermined displacement distance of the plunger into the medicament container.

17. The injection device of claim 9, wherein the deformable chock is arranged to expand upon receiving the chamfered head, thereby to grip walls of the medicament container.

\* \* \* \* \*